(12) United States Patent
Sampson et al.

(10) Patent No.: US 7,291,471 B2
(45) Date of Patent: Nov. 6, 2007

(54) CLEAVABLE OLIGONUCLEOTIDE ARRAYS

(75) Inventors: Jeffrey R. Sampson, San Francisco, CA (US); Joel Myerson, Berkeley, CA (US)

(73) Assignee: Agilent Technologies, Inc., Santa Clara, CA (US)

( * ) Notice: Subject to any disclaimer, the term of this patent is extended or adjusted under 35 U.S.C. 154(b) by 157 days.

(21) Appl. No.: 11/284,495

(22) Filed: Nov. 21, 2005

(65) Prior Publication Data
US 2007/0117101 A1 May 24, 2007

(51) Int. Cl.
*C12Q 1/68* (2006.01)
*C12M 3/00* (2006.01)
*C07H 21/00* (2006.01)

(52) U.S. Cl. .................. 435/6; 435/287.2; 536/25.3

(58) Field of Classification Search ............... 435/6, 435/287.2; 536/25.3
See application file for complete search history.

(56) References Cited

U.S. PATENT DOCUMENTS 5,143,854 A * 9/1992 Pirrung et al. ............ 436/518
5,449,754 A * 9/1995 Nishioka ................... 530/334
5,843,655 A * 12/1998 McGall ......................... 435/6
6,140,135 A * 10/2000 Landegren et al. ......... 436/518
6,699,668 B1 * 3/2004 Schmidt et al. ................. 435/6
7,026,114 B1 * 4/2006 Barone et al. ................. 435/6
7,122,303 B2 * 10/2006 Delenstarr et al. ............. 435/6

FOREIGN PATENT DOCUMENTS

WO    WO 98/41531    * 10/1998

OTHER PUBLICATIONS

Lipshutz et al., Using Oligonucleotide probe arrays to access genetic diversity. Biotechniques 19(3) 442-447 (1995).*
Blanchard et al., High-density oligonucleotide arrays. Biosensors & Bioelectronics 11(6/7) : 687-690 (1996).*
Pon et al., Linker phosphoramidite reagents for the attachment of the first nucleoside to underivatized solid-phase supports. Nucleic Acids Research 32(2) :623-631 (2004).*
Pease et al., Light-generated oligonucleotide arrays for rapid DNA sequence analysis. PNAS 91 : 5022-5026 (1994).*

* cited by examiner

*Primary Examiner*—Ethan Whisenant

(57) ABSTRACT

Oligonucleotide arrays having features that include cleavable oligonucleotides are disclosed, as well as methods of making such arrays. Methods of synthesizing an oligonucleotide on a surface of a substrate are described.

21 Claims, 2 Drawing Sheets

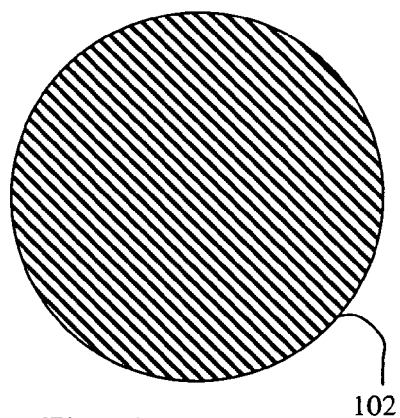
Fig._1
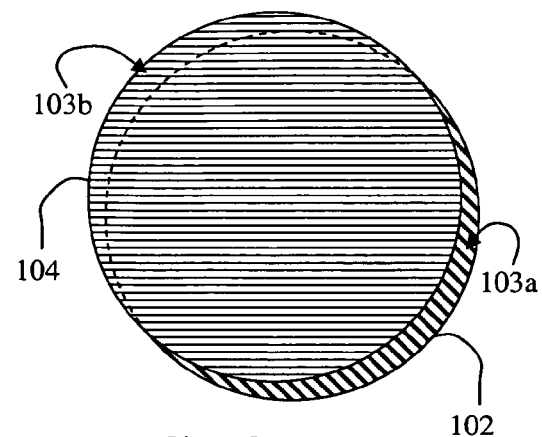
Fig._2
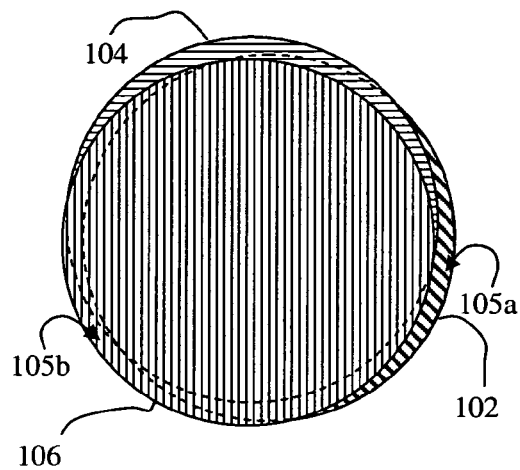
Fig._3
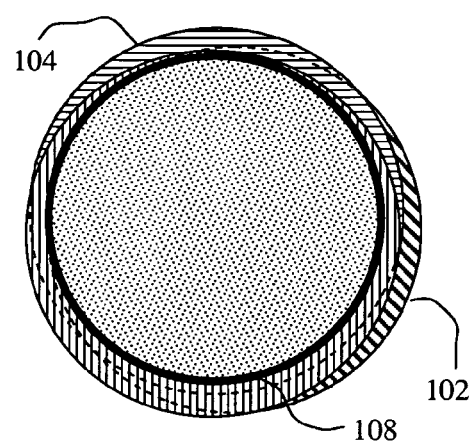
Fig._4
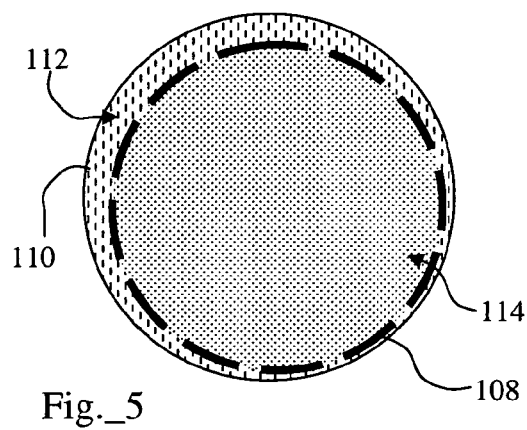
Fig._5
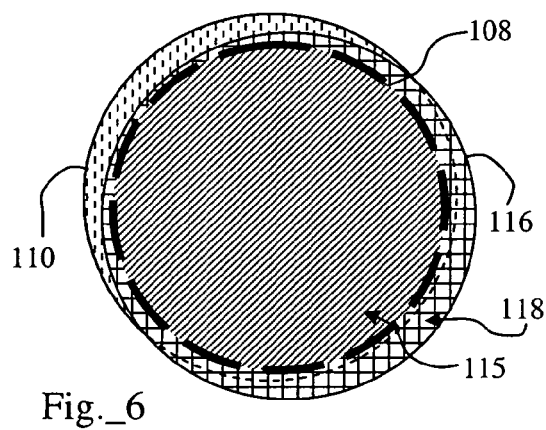
Fig._6

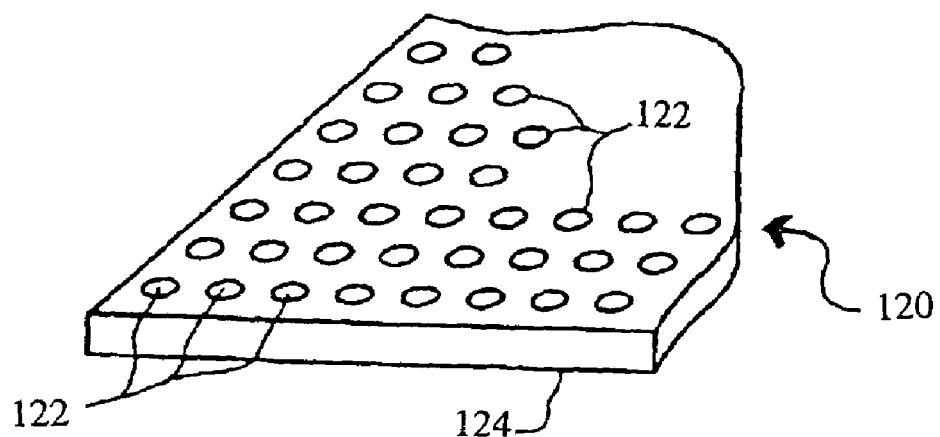
Fig._7
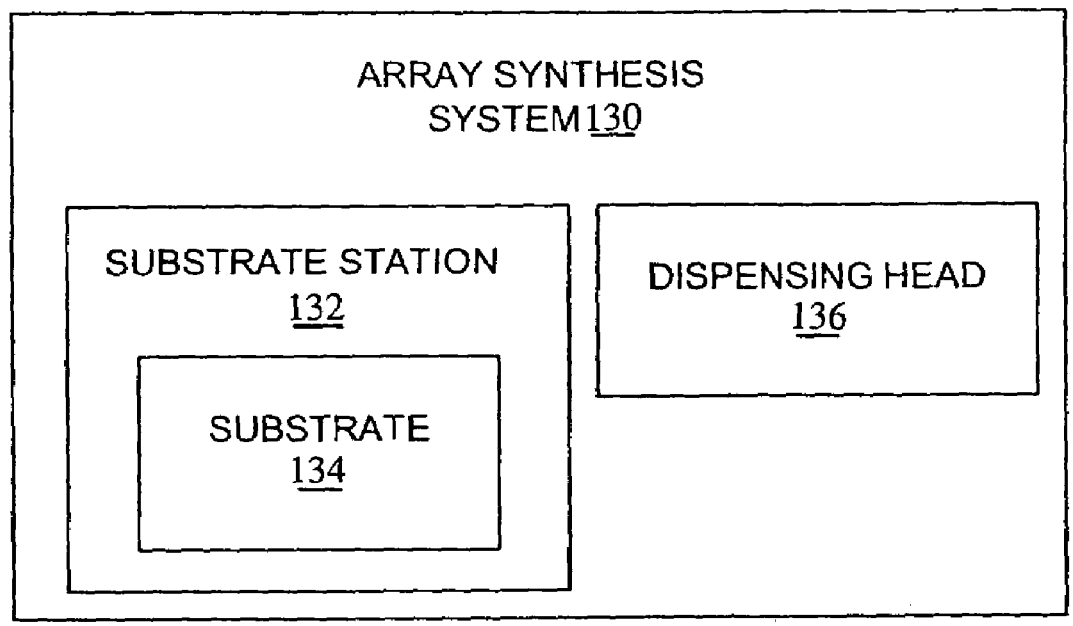
Fig._8

CLEAVABLE OLIGONUCLEOTIDE ARRAYS

DESCRIPTION

1. Field of the Invention

The invention relates generally to chemical synthesis methods. More specifically, the invention relates to methods of synthesizing polymers, e.g. polynucleotides.

2. Background of the Invention

Known methods of fabricating biopolymer arrays include in situ synthesis methods or deposition of the previously obtained biopolymers. The in situ synthesis methods include those described in U.S. Pat. No. 5,449,754 for synthesizing peptide arrays, as well as WO 98/41531 and the references cited therein for synthesizing polynucleotides (specifically, DNA). Such in situ synthesis methods can be basically regarded as iterating the sequence of: (a) depositing droplets of a protected monomer onto predetermined locations on a substrate to link with either a suitably activated substrate surface or with a previously deposited, deprotected monomer; (b) deprotecting the deposited monomer so that it can now react with a subsequently deposited protected monomer; and (c) depositing another protected monomer for linking. Different monomers may be deposited at different regions on the substrate during any one iteration so that the different regions of the completed array will have different desired biopolymer sequences. One or more intermediate further steps may be required in each iteration, such as oxidation and washing steps. The deposition methods basically involve depositing biopolymers at predetermined locations on a substrate which are suitably activated such that the biopolymers can link thereto. Biopolymers of different sequence may be deposited at different regions of the substrate to yield the completed array. Washing or other additional steps may also be used.

Large numbers of small amounts of individual oligonucleotides can be synthesized in array format and cleaved off the surface (see Pon (2004) Nucl. Acids Res. 32:623; Pon (2001) Tetrah. Lett. 42:8943; and Cuppoletti WO2004059010). Libraries of oligonucleotides prepared on arrays have been used for assembly of long sequences of DNA, e.g. genes. For some applications, such as gene assembly, it is important that the oligonucleotides be synthesized as pure as possible.

A need still remains for further methods of reducing error sequences in polynucleotide synthesis.

SUMMARY OF THE INVENTION

The invention addresses the aforementioned deficiencies in the art, and provides subject oligonucleotide arrays having features that include cleavable oligonucleotides. In certain embodiments, a subject oligonucleotide array includes a substrate having a surface and a plurality of features on the substrate. Each feature of the plurality of features includes A) a first population of oligonucleotides bound via a cleavable linker moiety to the surface, and B) a second population of oligonucleotides bound to the surface other than through said cleavable linker moiety. The first population of oligonucleotides defines an interior area of each feature. The second population of oligonucleotides defines an edge area of each feature, the edge area substantially surrounding the interior area.

In certain embodiments, a method of synthesizing an oligonucleotide on a surface of a substrate is provided. The method includes: a) covalently binding a cleavable linker moiety to the surface, the cleavable linker moiety defining an interior area on the surface, b) covalently binding a nucleotide moiety to the surface, the nucleotide moiety defining a combined area on the surface, wherein the combined area includes the interior area and an edge area substantially surrounding the interior area, wherein the nucleotide moiety in the interior area is bound to the surface via the cleavable linker moiety, wherein the nucleotide moiety in the edge area is bound to the surface other than via the cleavable linker moiety; and c) repeating b) as necessary to result in synthesis of the oligonucleotide on the surface.

Additional objects, advantages, and novel features of this invention shall be set forth in part in the descriptions and examples that follow and in part will become apparent to those skilled in the art upon examination of the following specifications or may be learned by the practice of the invention. The objects and advantages of the invention may be realized and attained by means of the instruments, combinations, compositions and methods particularly pointed out in the appended claims.

BRIEF DESCRIPTION OF THE DRAWINGS

These and other features of the invention will be understood from the description of representative embodiments of the method herein and the disclosure of illustrative apparatus for carrying out the method, taken together with the Figures, wherein FIG. 1 schematically illustrates a feature of an array.

FIG. 2 also schematically illustrates a feature of an array.

FIG. 3 also schematically illustrates a feature of an array.

FIG. 4 schematically illustrates a feature of an array having a cleavable linker moiety.

FIG. 5 schematically illustrates a feature of an array having a cleavable linker moiety.

FIG. 6 schematically illustrates a feature of an array having a cleavable linker moiety.

FIG. 7 depicts an array having a number of array features.

FIG. 8 schematically illustrates an array synthesis system.

To facilitate understanding, identical reference numerals have been used, where practical, to designate corresponding elements that are common to the Figures. Figure components are not drawn to scale.

DETAILED DESCRIPTION

Before the invention is described in detail, it is to be understood that unless otherwise indicated this invention is not limited to particular materials, reagents, reaction materials, manufacturing processes, or the like, as such may vary. It is also to be understood that the terminology used herein is for purposes of describing particular embodiments only, and is not intended to be limiting. It is also possible in the present invention that steps may be executed in different sequence where this is logically possible.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

It must be noted that, as used in the specification and the appended claims, the singular forms "a," "an" and "the" include plural referents unless the context clearly dictates otherwise. Thus, for example, reference to "a ligand" includes a plurality of ligands. It is further noted that the claims may be drafted to exclude any optional element. As such, this statement is intended to serve as antecedent basis for use of such exclusive terminology as "solely", "only" and the like in connection with the recitation of claim elements, or the use of a "negative" limitation. In this specification and in the claims that follow, reference will be made to a number of terms that shall be defined to have the following meanings unless a contrary intention is apparent.

As used herein, polynucleotides include single or multiple stranded configurations, where one or more of the strands may or may not be completely aligned with another. The terms "polynucleotide" and "oligonucleotide" shall be generic to polydeoxyribonucleotides (containing 2-deoxy-D-ribose), to polyribonucleotides (containing D-ribose), to any other type of polynucleotide which is an N-glycoside of a purine or pyrimidine base, and to other polymers in which the conventional backbone has been replaced with a non-naturally occurring or synthetic backbone or in which one or more of the conventional bases has been replaced with a non-naturally occurring or synthetic base.

A "nucleotide moiety" refers to a subunit of a nucleic acid (whether DNA or RNA or analogue thereof) which includes a phosphate group, a sugar group and a nitrogen containing base, as well as analogs of such subunits. A nucleotide moiety typically is part of a larger molecule, e.g. an activated nucleotide monomer used for synthesizing oligonucleotides, further e.g an oligonucleotide synthesized using such activated nucleotide monomers.

A "nucleoside" references a nucleic acid subunit including a sugar group and a nitrogen containing base. It should be noted that the term "nucleotide" is used herein to describe embodiments of the disclosure, but that one skilled in the art would understand that the term "nucleoside" and "nucleotide" are interchangeable in most instances. One skilled in the art would have the understanding that additional modification to the nucleoside may be necessary and one skilled in the art has such knowledge. A "nucleoside moiety" refers to a moiety having a sugar group and a nitrogen containing base (as in a nucleoside) as a portion of a larger molecule, such as in a polynucleotide, oligonucleotide, or nucleoside phosphoramidite.

A "nucleotide monomer" refers to a molecule which is not incorporated in a larger oligo- or poly-nucleotide chain and which corresponds to a single nucleotide subunit; nucleotide monomers can also have activating or protecting groups, if such groups are necessary for the intended use of the nucleotide monomer.

A "polynucleotide intermediate" references a molecule occurring between steps in chemical synthesis of a polynucleotide, where the polynucleotide intermediate is subjected to further reactions to get the intended final product (e.g., a phosphite intermediate, which is oxidized to a phosphate in a later step in the synthesis), or a protected polynucleotide, which is then deprotected.

An "oligonucleotide" generally refers to a nucleotide multimer of about 2 to 100 nucleotides in length, while a "polynucleotide" includes a nucleotide multimer having any number of nucleotides.

It will be appreciated that, as used herein, the terms "nucleoside" and "nucleotide" will include those moieties which contain not only the naturally occurring purine and pyrimidine bases, e.g., adenine (A), thymine (T), cytosine (C), guanine (G), or uracil (U), but also modified purine and pyrimidine bases and other heterocyclic bases which have been modified (these moieties are sometimes referred to herein, collectively, as "purine and pyrimidine bases and analogs thereof"). Such modifications include, e.g., methylated purines or pyrimidines, acylated purines or pyrimidines, and the like, or the addition of a protecting group such as acetyl, difluoroacetyl, trifluoroacetyl, isobutyryl, benzoyl, or the like. The purine or pyrimidine base can also be an analog of the foregoing; suitable analogs will be known to those skilled in the art and are described in the pertinent texts and literature. Common analogs include, but are not limited to, 1-methyladenine, 2-methyladenine, N6-methyladenine, N6-isopentyladenine, 2-methylthio-N6-isopentyladenine, N,N-dimethyladenine, 8-bromoadenine, 2-thiocytosine, 3-methylcytosine, 5-methylcytosine, 5-ethylcytosine, 4-acetylcytosine, 1-methylguanine, 2-methylguanine, 7-methylguanine, 2,2-dimethylguanine, 8-bromoguanine, 8-chloroguanine, 8-aminoguanine, 8-methylguanine, 8-thioguanine, 5-fluorouracil, 5-bromouracil, 5-chlorouracil, 5-iodouracil, 5-ethyluracil, 5-propyluracil, 5-methoxyuracil, 5-hydroxymethyluracil, 5-(carboxyhydroxymethyl)uracil, 5-(methylaminomethyl)uracil, 5-(carboxymethylaminomethyl)-uracil, 2-thiouracil, 5-methyl-2-thiouracil, 5-(2-bromovinyl)uracil, uracil-5-oxyacetic acid, uracil-5-oxyacetic acid methyl ester, pseudouracil, 1-methylpseudouracil, queosine, inosine, 1-methylinosine, hypoxanthine, xanthine, 2-aminopurine, 6-hydroxyaminopurine, 6-thiopurine and 2,6-diaminopurine.

An "internucleotide bond" refers to a chemical linkage between two nucleoside moieties, such as a phosphodiester linkage in nucleic acids found in nature, or such as linkages well known from the art of synthesis of nucleic acids and nucleic acid analogues. An internucleotide bond can include a phospho or phosphite group, and can include linkages where one or more oxygen atoms of the phospho or phosphite group are either modified with a substituent or replaced with another atom, e.g. a sulfur atom, or the nitrogen atom of a mono- or di-alkyl amino group.

An "array", unless a contrary intention appears, includes any one, two or three dimensional arrangement of addressable regions bearing a particular chemical moiety or moieties (for example, polynucleotide sequences) associated with that region. An array is "addressable" in that it has multiple regions of different moieties (for example, different polynucleotide sequences) such that a region (a "feature" or "spot" of the array) is at a particular predetermined location (an "address") on the array. An "array layout" refers to one or more characteristics of the array, such as feature positioning, feature size, and some indication of a moiety at a given location.

A "pulse jet" is a device which can dispense drops in the formation of an array. Pulse jets operate by delivering a pulse of pressure to liquid adjacent an outlet or orifice such that a drop will be dispensed therefrom (for example, by a piezoelectric or thermoelectric element positioned in a same chamber as the orifice).

A "phospho" group includes a phosphodiester, phosphotriester, and H-phosphonate groups. In the case of either a phospho or phosphite group, a chemical moiety other than a substituted 5-membered furyl ring can be attached to O of the phospho or phosphite group which links between the furyl ring and the P atom.

A "protecting group" is used in the conventional chemical sense to reference a group, which reversibly renders unreactive a functional group under specified conditions of a desired reaction. After the desired reaction, protecting groups can be removed to deprotect the protected functional group. All protecting groups should be removable (and hence, labile) under conditions which do not degrade a substantial proportion of the molecules being synthesized. In contrast to a protecting group, a "capping group" permanently binds to a segment of a molecule to prevent any further chemical transformation of that segment.

A "hydroxyl protecting group" refers to a protecting group where the protected group is a hydroxyl. A "reactive-site hydroxyl" is the terminal 5'-hydroxyl during 3'-5' polynucleotide synthesis and is the 3'-hydroxyl during 5'-3' polynucleotide synthesis. An "acid labile protected hydroxyl" is a hydroxyl group protected by a protecting group that can be removed by acidic conditions. Similarly, an "acid labile protecting group" is a protecting group that can be removed by acidic conditions. Preferred protecting groups that are capable of removal under acidic conditions ("acid-labile protecting groups") include those such as tetrahydropyranyl groups, e.g. tetrahydropyran-2-yl and 4-methoxytetrahydropyran-2-yl; an arylmethyl group with n aryl groups (where n=1 to 3) and 3-n alkyl groups such as an optionally substituted trityl group, for example a monomethoxytrityl for oligoribonucleotide synthesis and a dimethoxytrityl for oligodeoxyribonucleotide synthesis, pixyl; isobutyloxycarbonyl; t-butyl; and dimethylsilyl. A trityl group is a triphenylmethyl group. Suitable protecting groups are described in "Protective Groups in Organic Synthesis" by T. W. Green, Wiley Interscience.

"Moiety" and "group" are used to refer to a portion of a molecule, typically having a particular functional or structural feature, e.g. a linking group (a portion of a molecule connecting two other portions of the molecule), or an ethyl moiety (a portion of a molecule with a structure closely related to ethane). A "moiety" or "group" includes both substituted and unsubstituted forms. Typical substituents include one or more lower alkyl, any halogen, hydroxy, or aryl, or optionally substituted on one or more available carbon atoms with a nonhydrocarbyl substituent such as cyano, nitro, halogen, hydroxyl, or the like.

"Bound" may be used herein to indicate direct or indirect attachment. In the context of chemical structures, "bound" (or "bonded", or "bind", or "binding", or like term) may refer to the existence of a chemical bond directly joining two moieties or indirectly joining two moieties (e.g. via a linking group or any other intervening portion of the molecule). The chemical bond may be a covalent bond, an ionic bond, a coordination complex, hydrogen bonding, van der Waals interactions, or hydrophobic stacking, or may exhibit characteristics of multiple types of chemical bonds. In certain instances, "bound" includes embodiments where the attachment is direct and also embodiments where the attachment is indirect. "Free," as used in the context of a moiety that is free, indicates that the moiety is available to react with or be contacted by other components of the solution in which the moiety is a part. Two moieties "directly bound" to each other are joined to each other without any intervening moiety. As used herein, when a moiety (e.g. a nucleotide moiety or an oligonucleotide moiety) is bound to the substrate "other than via the cleavable linker moiety", it means that the moiety is bound to the substrate, but the moiety in not bound via a cleavable linker moiety, i.e. there is no cleavable linker moiety linking the moiety to the surface. The moiety may be bound directly to the surface, or may be indirectly bound to the surface via an intervening moiety, such as a non-cleavable linker or a portion of an oligonucleotide being synthesized using a method described herein. Examples of such intervening moieties include those referenced in the art as 'tethers', 'linkers', 'stilts', and such are well known and need not be described in further detail here.

"Linkage" as used herein refers to a first moiety bonded to two other moieties, wherein the two other moieties are linked via the first moiety. Typical linkages include ether (—O—), oxo (—C(O)—), amino (—NH—), amido (—N—C(O)—), thio (—S—), phospho (—P—), ester (—O—C(O)—).

"Functionalized" references a process whereby a material is modified to have a specific moiety bound to the material, e.g. a molecule or substrate is modified to have the specific moiety; the material (e.g. molecule or support) that has been so modified is referred to as a functionalized material (e.g. functionalized molecule or functionalized support).

"Optional" or "optionally" means that the subsequently described circumstance may or may not occur, so that the description includes instances where the circumstance occurs and instances where it does not. For example, the phrase "optionally substituted" means that a non-hydrogen substituent may or may not be present, and, thus, the description includes structures wherein a non-hydrogen substituent is present and structures wherein a non-hydrogen substituent is not present. At various points herein, a moiety may be described as being present zero or more times: this is equivalent to the moiety being optional and includes embodiments in which the moiety is present and embodiments in which the moiety is not present. If the optional moiety is not present (is present in the structure zero times), adjacent groups described as linked by the optional moiety are linked to each other directly. Similarly, a moiety may be described as being either (1) a group linking two adjacent groups, or (2) a bond linking the two adjacent groups: this is equivalent to the moiety being optional and includes embodiments in which the moiety is present and embodiments in which the moiety is not present. If the optional moiety is not present (is present in the structure zero times), adjacent groups described as linked by the optional moiety are linked to each other directly.

The conventional techniques of oligonucleotide synthesis basically involve an iterative cycle including four separate steps: (a) coupling a selected nucleoside which also has a protected hydroxy group, through a phosphite linkage to a functionalized support in the first iteration, or to a nucleoside bound to the substrate (e.g., the nucleoside-modified substrate) in subsequent iterations; (b) optionally, blocking unreacted hydroxyl groups on the substrate bound nucleoside; (c) oxidizing the phosphite linkage of step (a) to form a phosphate linkage; and (d) removing the protecting group ("deprotection") from the now substrate-bound nucleoside coupled in step (a), to generate a reactive site for the next cycle of these steps. The functionalized support (in the first cycle) or deprotected coupled nucleoside (in subsequent cycles) provides a substrate-bound moiety with an available active site (e.g. a chemically reactive group such as hydroxyl, e.g. a 3'- or 5'-OH) for forming the phosphite linkage with a next nucleoside to be coupled in step (a). Final deprotection of nucleoside bases can be accomplished using alkaline conditions, such as ammonium hydroxide, in a known manner.

The in situ method for fabricating an oligonucleotide array typically follows, at each of the multiple different addresses at which features are to be formed, the same conventional iterative sequence used in forming polynucleotides on a support by means of known chemistry. During array fabrication, different monomers can be deposited at different addresses on the substrate during any one iteration so that the different features of the completed array will have different desired polynucleotide sequences. The coupling can be performed by depositing drops of an activator and phosphoramidite at the specific desired feature locations for the array. One or more intermediate further steps can be required in each iteration, such as the conventional oxidation and washing steps.

The foregoing methods of preparing polynucleotides are well known and described in detail, for example, in Caruthers, Science 230: 281-285, 1985; Itakura et al., Ann. Rev. Biochem. 53: 323-356; Hunkapillar et al., Nature 310: 105-110, 1984; and in "Synthesis of Oligonucleotide Derivatives in Design and Targeted Reaction of Oligonucleotide Derivatives, CRC Press, Boca Raton, Fla., pages 100 et seq., U.S. Pat. No. 4,415,732, U.S. Pat. No. 4,458,066, U.S. Pat. No. 4,500,707, U.S. Pat. No. 5,153,319, U.S. Pat. No. 5,869,643, EP 0294196, and elsewhere. The phosphoramidite and phosphite triester approaches are most broadly used, but other approaches include the phosphodiester approach, the phosphotriester approach and the H-phosphonate approach. Such approaches are described in Beaucage et al., Tetrahedron (1992) 12:2223-2311. A more recent approach for synthesis of polynucleotides is described in U.S. Pat. No. 6,222,030 B1 to Dellinger et al., issued Apr. 24, 2001.

Oligonucleotide synthesis using phosphoramidate chemistry is capable of extremely high efficiencies, in excess of 99% yield per synthesis cycle under ideal conditions. Synthesis in an array format presents different problems when compared to synthesis in the more typical cartridge or column format.

In oligonucleotide synthesis using inkjet technology, in particular, the ability to reproducibly deliver phosphoramidites in exactly the same place each time can dramatically affect the purity of the final product. If the inkjet heads that deliver the four different monomers are not in perfect registration, the growing oligonucleotide can contain regular regions of incorrect sequence. Similarly, variability in the position of deposited droplet of any of the monomers can cause defects in the oligonucleotide sequence. Even if the registration of the four inkjet heads is perfect and there is very low variability in the positions of the deposited droplets, errors in synthesis can still occur at the edges of a given feature due to slight variations in size or spreading of the droplet, or reagent diffusion within the droplet.

FIGS. 1-3 illustrate synthesis of an oligonucleotide at a feature of an array. In FIG. 1, a droplet containing an activated nucleotide monomer (e.g. a nucleoside phosphoramidite) is deposited at the feature, resulting in an area 102 that receives the activated nucleotide monomer, resulting in attachment of a nucleotide subunit to establish a nascent oligonucleotide at the feature. FIG. 2 shows the result of another cycle of oligonucleotide synthesis, in which another droplet containing an activated nucleotide monomer is deposited at the feature, resulting in an area 104 that receives the activated nucleotide monomer, resulting in attachment of a nucleotide subunit to lengthen the nascent oligonucleotide at the feature. For the most part, the area 104 covers the area 102, but there is a relatively small portion 103a of area 102 missed around the edge. The dashed line in FIG. 2 delineates the area 102 which is covered by area 104, thus illustrating that application of the latter droplet may also leave a small portion 103b of area 104 extending beyond the area 102.

FIG. 3 shows the result of another cycle of oligonucleotide synthesis, in which another droplet containing an activated nucleotide monomer is deposited at the feature, resulting in an area 106 that receives the activated nucleotide monomer, resulting in attachment of a nucleotide subunit to lengthen the nascent oligonucleotide at the feature. In FIG. 3 it is the area 106 which, for the most part, covers the area 104, and there is a relatively small portion 105a of areas 102 and 104 around the edge which is not covered by area 106. Also, area 106 may have a small portion 105b that extends beyond the previous areas 102 and 104. In FIG. 2 and FIG. 3, oligonucleotides synthesized in the edge area will have errors from the occasional lapses of coverage such as illustrated in FIG. 2 and FIG. 3.

Referring now to FIG. 4, an embodiment of the present invention is illustrated. A droplet containing an activated cleavable linker moiety is deposited at the feature, resulting in an area 108 that receives the activated cleavable linker moiety, resulting in attachment of a cleavable linker moiety to establish a site from which synthesis of a cleavable oligonucleotide may commence. The cleavable linker moiety has an available active site for binding to the activated nucleotide monomer. In this regard, "activated" references an ability to react with an active site to result in a covalent bond between a newly added nucleotide subunit and the moiety having the active site, e.g. a 5'- or 3'-OH of growing oligonucleotide, a cleavable linker moiety, or the substrate. Note that the area 108 is smaller than any of areas 102, 104, or 106 and typically covers an interior area of the feature surrounded by an edge area of the feature that includes the edges of the areas 102, 104, 106.

In further iterations of the oligonucleotide synthesis cycle, droplets containing activated nucleotide monomers are deposited at the feature. The droplets typically are of a size similar to the previous droplets containing activated nucleotide monomer, i.e. they are larger than the droplet containing activated cleavable linker moiety and result in coverage of an area similar in size to areas 102, 104, and 106, i.e. larger than area 108. Typically, the area 108 defined by the cleavable linker moiety is completely covered during further cycles of oligonucleotide synthesis.

FIG. 5 illustrates an area 108 having a cleavable linker moiety attached to the surface, e.g. as described for FIG. 4. The heavy dotted line that denotes the area 108 indicates that area 108 is completely covered during further cycles of oligonucleotide synthesis. FIG. 5 shows the result after an iteration of the oligonucleotide synthesis cycle in which a droplet containing an activated nucleotide monomer is deposited at the feature, resulting in an area 110 that receives the activated nucleotide monomer, resulting in attachment of a nucleotide subunit to the cleavable linker at the feature. Area 110 includes area 114, at which the nucleotide subunit is bound to the surface via the cleavable linker moiety, and area 112, at which the nucleotide subunit is bound to the surface other than via the cleavable linker moiety. Area 114 is coincident with 108.

FIG. 6 shows the result of another cycle of oligonucleotide synthesis, in which another droplet containing an activated nucleotide monomer is deposited at the feature, resulting in an area 116 that receives the activated nucleotide monomer, resulting in attachment of a nucleotide subunit to lengthen the nascent oligonucleotide at the feature. Again, the heavy dotted line that denotes the area 108 indicates that area 108 is completely covered by the droplet of activated nucleotide monomer during the cycle of oligonucleotide synthesis. In FIG. 6 area 116 covers the area 108. Area 116 includes area 115, at which the nucleotide subunit is bound to the surface via the cleavable linker moiety (also via the previously deposited nucleotide subunit), and area 118, at which the nucleotide subunit is bound to the surface other than via the cleavable linker moiety. Area 115 is coincident with 108. In FIG. 5 and FIG. 6, oligonucleotides synthesized in the edge area will have errors from the occasional lapses of coverage such as illustrated in FIG. 5 and FIG. 6.

Due to the slight mis-alignment of droplet placement during each iteration of the synthesis cycle, an edge area is defined around the interior area (the interior area defined by the presence of the cleavable linker moiety, e.g. area 108). After multiple rounds of synthesis, the edge area is defined as the area outside of the interior area that has oligonucleotide bound to the substrate other than via the cleavable linker moiety. For example, the edge area is the area covered by the droplets of activated nucleotide monomers deposited on the substrate during the multiple rounds of synthesis exclusive of the area defined by the cleavable linker moiety. In certain embodiments the edge area substantially surrounds the interior area, i.e. a part of the perimeter of the interior area is not directly adjacent a part of the edge area (e.g. a part of the perimeter of the interior area is directly adjacent a part of the substrate surface that is not a portion of the interior area or the edge area). In this regard, "substantially surrounds" means that at least about 70% (e.g at least about 80%, at least about 90%, at least about 95%) of the perimeter of the interior area is directly adjacent a part of the edge area. In typical embodiments, the edge area of a feature completely surrounds the interior area of that feature, i.e. every part of the perimeter of the interior area is directly adjacent a part of the edge area.

The iteration of the synthesis cycle continues as necessary until a cleavable oligonucleotide having the desired sequence is synthesized. The synthesis process results in an oligonucleotide (e.g. a 'first population of oligonucleotides') bound to the substrate via the cleavable linker moiety. The synthesis process also results in synthesis of oligonucleotide (e.g. a 'second population of oligonucleotides') that is not bound to the substrate via the cleavable linker, e.g. in the edge area described above. As explained, significant errors in synthesis occur at the edge of the area of the feature due to inexact coverage. The area 108 defined by the cleavable linker moiety is an interior area of the feature and excludes the surrounding edge area of the feature. The cleavable oligonucleotides will thus tend to have lower incidence of errors in synthesis.

In particular embodiments, the oligonucleotides bound at the interior area of a feature (e.g. bound to the surface via the cleavable linker moiety) constitutes a lower percentage (on a mol/mol basis) of failure sequences than the oligonucleotides bound at the edge area. The percentage of failure sequences may be calculated as follows: the mole quantity of oligonucleotides that are failure sequences is divided by the total mole quantity of oligonucleotides estimated to be bound to the given area (e.g. the interior area or the edge area). The numeric result is then multiplied by 100% to be expressed as a percentage. The percentage of failure sequences of the oligonucleotides bound at the edge area is calculated using the same intended sequence. The percentages can then be compared. In this regard, a failure sequence is an oligonucleotide by-product of the oligonucleotide synthesis process that does not have the intended sequence. The intended sequence is the known sequence used in synthesizing the oligonucleotide on the substrate, that is, it is the goal of the synthesis.

With lengthy oligonucleotide sequences, e.g. those over 30 nucleotides long, e.g. those over 40 nucleotides long, e.g. those over 50 nucleotides long, the percentage of failure sequences may be calculated as follows: the mole quantity of oligonucleotides that fail to meet a quality standard (e.g. fewer than two or three omitted nucleotides in a 60-mer sequence) is divided by the total mole quantity of oligonucleotides estimated to be bound to the given area (e.g. the interior area or the edge area). The numeric result is then multiplied by 100% to be expressed as a percentage. The percentage of failure sequences of the oligonucleotides bound at the edge area is calculated using the same quality standard. The percentages can then be compared.

The percentage of failure sequences may be demonstrated, for example, by conducting a comparative experiment in which a 'test feature' is made on an array substrate. In the comparative experiment, the test feature is made using the subject method described herein, with the exception that the cleavable linker moiety is applied over a larger area to include all of the edge area, i.e. the cleavable linker moiety bound to the substrate defines a larger area than is contacted with the droplets of activated nucleotide monomer during the successive iterations of the synthesis cycle. In this manner, all the oligonucleotide molecules synthesized at the feature are cleavable from the substrate and can be analyzed to determine the percentage of failure sequences and the percentage of oligonucleotide molecules having the intended sequence. This information would be compared to the results of similar analysis of oligonucleotides released from the interior area of a subject feature as described herein. The length of the released oligonucleotides provides an estimate of the oligonucleotides having the intended sequence, especially in embodiments in which each iteration of the synthesis cycle includes a capping step.

Alternatively, two cleavable linkers (e.g. having orthogonal cleavage conditions) may be used, the first applied over a larger area to include all of the edge area, and the second applied to define the interior area. The second cleavable linker would be cleaved to release the oligonucleotides bound via the cleavable linker defining the interior area, and the released oligonucleotides would be recovered. Then the first cleavable linker would be cleaved to release the edge oligonucleotides, and the released oligonucleotides would be recovered. The two sets of released oligonucleotides would then be analyzed to determine failure rates.

As mentioned, in particular embodiments, the oligonucleotides bound at the interior area of a feature (e.g. bound to the surface via the cleavable linker moiety) constitutes a lower percentage (on a mol/mol basis) of failure sequences than the oligonucleotides bound at the edge area. In certain embodiments, the percentage of failure sequences of oligonucleotides bound at the edge area is at least 110% (e.g. at least 120%, at least 130%, at least 140%, at least 150%, at least 200%, at least 300%), of the percentage of failure sequences of oligonucleotides bound at the interior area. This percentage is calculated by dividing the (the percentage of failure sequences of oligonucleotides bound at the edge area) by (the percentage of failure sequences of oligonucleotides bound at the interior area), then multiplying by 100% to express as a percentage.

As indicated in FIGS. 1-3, in certain embodiments, at least one round of synthesis is performed before the cleavable linker moiety is bound to the surface of the substrate. In some such embodiments, a droplet containing an activated nucleotide monomer (e.g. a nucleoside phosphoramidite) is deposited at the feature, resulting in an area 102 that receives the activated nucleotide monomer, resulting in attachment of a nucleotide subunit to establish a nascent oligonucleotide at the feature. In some embodiments, at least two (e.g. at least 3, at least 4, at least 5) and up to 8 or more (e.g. up to 10, up to 15, up to 20, or more) rounds of synthesis occur at a feature prior to attachment of a cleavable linker moiety at the feature. This provides an established 'bed' of oligonucleotides on the surface of the substrate before attachment of the linker and synthesis of the cleavable oligonucleotides. The 'bed' of oligonucleotides may provide an improved surface for more effective coupling of activated nucleotide monomers in subsequent rounds of synthesis. Thus, in certain embodiments the cleavable linker moiety is attached to the substrate via a single nucleotide moiety or via an oligonucleotide moiety that is at least 2 nt (nucleotides) long (e.g. at least 3 nt long, at least 4 nt long, at least 5 nt long) and is up to about 20 nt long (e.g. up to about 8 nt long, up to about 10 nt long, up to about 15 nt long) or longer. In other embodiments, the cleavable linker moiety is bound to surface directly (without an intervening oligonucleotide) or via a single nucleotide subunit.

As described herein, each round of the synthesis cycle typically includes contacting a surface of a substrate with a droplet containing a nucleotide moiety, e.g. an activated nucleotide monomer, under conditions that result in the nucleotide moiety being covalently bound to an available reactive site moiety bound to the substrate, such as a 3'- or 5'-hydroxyl moiety of a deprotected nascent oligonucleotide. In certain embodiments, during each round of the synthesis cycle a droplet containing an activated nucleotide monomer is deposited at a feature on the substrate, resulting in an area that receives the activated nucleotide monomer, resulting in attachment of a nucleotide subunit to lengthen the nascent oligonucleotide at the feature. In typical embodiments, each round of the synthesis cycle includes oxidizing an intermediate phosphite to a phospho group, deprotecting the nucleotide moiety (e.g. removing a protecting group from a nucleotide moiety bound to the substrate), as well as (optionally) performing a capping (or blocking) reaction. In typical embodiments, the nucleotide moiety includes a protecting group, e.g. a 3'- or 5'-hydroxyl protecting group that gets removed in a later part of the synthesis cycle, as described herein. In certain embodiments, certain iterations of the synthesis cycle include contacting a surface of a substrate with a droplet containing an activated nucleotide dimer, trimer, or tetramer. Modification of the typical synthesis cycle to use such activated nucleotide moieties (e.g. activated oligonucleotide moieties) is known in the art.

Accordingly, in certain embodiments, a method of synthesizing an oligonucleotide on a surface of a substrate is provided. The method includes:
  a) covalently binding a cleavable linker moiety to the surface, the cleavable linker moiety defining an interior area on the surface,
  b) covalently binding a nucleotide moiety to the surface, the nucleotide moiety defining a combined area on the surface, wherein the combined area includes the interior area and an edge area substantially surrounding the interior area, wherein the nucleotide moiety in the interior area is bound to the surface via the cleavable linker moiety, wherein the nucleotide moiety in the edge area is bound to the surface other than via the cleavable linker moiety; and
  c) repeating b) as necessary to result in synthesis of the oligonucleotide on the surface.

In particular embodiments, the subject method is performed at each site of a plurality of sites on the surface of the substrate to result in the synthesis of an oligonucleotide at each site of the plurality of sites. Typically, the subject method is performed at each site of at least about 10 sites, e.g. at least about 50 sites, at least about 100 sites, at least about 200 sites, at least about 500 sites, at least about 1000 sites, at least about 2000 sites, or more. In particular embodiments, the subject method is performed at each site of as many as about 5000 sites, e.g. as many as about 10,000 sites, as many as about 20,000 sites, as many as about 50,000 sites, as many as about 100,000 sites, or more. In such embodiments, the method may result in synthesis of at least about 10 different oligonucleotides, e.g. at least about 50 different oligonucleotides, at least about 100 different oligonucleotides, at least about 200 different oligonucleotides, at least about 500 different oligonucleotides, at least about 1000 different oligonucleotides, at least about 2000 different oligonucleotides, or more. In typical embodiments, the method may result in synthesis of as many as about 5000 different oligonucleotides, e.g. as many as about 10,000 different oligonucleotides, as many as about 20,000 different oligonucleotides, as many as about 50,000 different oligonucleotides, as many as about 100,000 different oligonucleotides, or more.

Each iteration of the synthesis cycle (i.e. each iteration of "b)", above) provides a corresponding combined area defined by the binding of the oligonucleotide moiety to the surface during said iteration of the synthesis cycle. In particular embodiments, for each iteration of the synthesis cycle, the interior area on the surface is at least about 10% of the corresponding combined area of the surface. (The combined area of the feature is the sum of the interior area of the feature and the edge area of the feature.) In some such embodiments, for each iteration of the synthesis cycle, the interior area on the surface is at least about 20%, e.g. at least about 30%, at least about 40%, at least about 50%, at least about 60%, at least about 70% of the corresponding combined area of the feature. In certain embodiments, for each iteration of the synthesis cycle, the interior area on the surface is up to about 75%, up to about 80%, up to about 85%, up to about 90%, up to about 95%, or more of the corresponding combined area of the feature.

In certain embodiments, an oligonucleotide array having features that include cleavable oligonucleotides is provided. In typical embodiments, the array includes a substrate having a surface and a plurality of features on the substrate. Each feature of the plurality of features includes A) a first population of oligonucleotides bound via a cleavable linker moiety to the surface, and B) a second population of oligonucleotides bound to the surface other than through said cleavable linker moiety. The first population of oligonucleotides defines an interior area of each feature. The second population of oligonucleotides defines an edge area of each feature, the edge area substantially surrounding the interior area. The first population of oligonucleotides is releasable (cleavable) from the substrate.

In particular embodiments of a subject oligonucleotide array, the interior area of each feature of the plurality of features is at least about 10% of the total defined area of the feature. (The total defined area of the feature is the sum of the interior area of the feature and the edge area of the feature.) In some such embodiments, the interior area of each feature of the plurality of features is at least about 20%, e.g. at least about 30%, at least about 40%, at least about 50%, at least about 60%, at least about 70% of the total defined area of the feature. In certain embodiments, the interior area of each feature of the plurality of features is up to about 75%, up to about 80%, up to about 85%, up to about 90%, up to about 95%, or more of the total defined area of the feature.

FIG. 7 illustrates an exemplary embodiment of an array in accordance with the present invention. The array 120 may contain any number of features 122 located on an array substrate 124. Each of the features may be formed on the substrate using in situ synthesis methods as described herein.

The array generally includes at least tens of features, usually at least hundreds, more usually thousands, and as many as a hundred thousand or more features. All of the features may be different, or some or all could be the same. Each feature carries a predetermined moiety or a predetermined mixture of moieties, such as a particular polynucleotide sequence or a predetermined mixture of polynucleotides. The features of the array can be arranged in any desired pattern (e.g. organized rows and columns of features, for example, a grid of features across the substrate surface); a series of curvilinear rows across the substrate surface (for example, a series of concentric circles or semi-circles of features, and the like). In particular embodiments, the array includes at least about 10 features, e.g. at least about 50 features, at least about 100 features, at least about 200 features, at least about 500 features, at least about 1000 features, at least about 2000 features, or more. In particular embodiments, the array 120 includes as many as about 5000 features, e.g. as many as about 10,000 features, as many as about 20,000 features, as many as about 50,000 features, as many as about 100,000 features or more.

In embodiments where very small feature sizes are desired, the density of features on the substrate can range from at least about ten features per square centimeter, or at least about 35 features per square centimeter, or at least about 100 features per square centimeter, and up to about 1000 features per square centimeter, up to about 10,000 features per square centimeter, or up to 100,000 features per square centimeter. Each feature carries a predetermined nucleotide sequence (which includes the possibility of mixtures of nucleotide sequences).

In array fabrication, the quantities of polynucleotide available are usually very small and expensive. Therefore, one embodiment of the invention provides for fabrication of arrays with large numbers of very small, closely spaced features. Arrays can be fabricated with features that can have widths (that is, diameter, for a round spot) in the range from a minimum of about 10 micrometers to a maximum of about 1.0 cm. In embodiments where very small spot sizes or feature sizes are desired, material can be deposited according to the invention in small spots whose width is in the range about 1.0 micrometer to 1.0 mm, usually about 5.0 micrometers to 0.5 mm, and more usually about 10 micrometers to 200 micrometers. Features that are not round generally have dimensions (e.g. surface area) in the same range as those given above for round features. Interfeature areas will typically (but not essentially) be present which do not carry any polynucleotide. It will be appreciated though, that the interfeature areas could be of various sizes and configurations.

In one embodiment, about 10 to 100 of such arrays can be fabricated on a single substrate (such as glass). In such embodiment, after the substrate has the polynucleotides on its surface, the substrate can be cut into substrate segments, each of which can carry one or two arrays. It will also be appreciated that there need not be any space separating arrays from one another. Where a pattern of arrays is desired, any of a variety of geometries can be constructed, including for example, organized rows and columns of arrays (for example, a grid of arrays, across the substrate surface), a series of curvilinear rows across the substrate surface (for example, a series of concentric circles or semi-circles of arrays), and the like.

The array substrate can take any of a variety of configurations ranging from simple to complex. Thus, the substrate could have generally planar form, as for example a slide or plate configuration, such as a rectangular or square or disc. In many embodiments, the substrate will be shaped generally as a rectangular solid, having a length in the range about 4 mm to 300 mm, usually about 4 mm to 150 mm, more usually about 4 mm to 125 mm; a width in the range about 4 mm to 300 mm, usually about 4 mm to 120 mm and more usually about 4 mm to 80 mm; and a thickness in the range about 0.01 mm to 5.0 mm, usually from about 0.1 mm to 2 mm and more usually from about 0.2 to 1 mm. The substrate surface onto which the polynucleotides are bound can be smooth or substantially planar, or have irregularities, such as depressions or elevations. The configuration of the array can be selected according to manufacturing, handling, and use considerations.

Suitable substrates can have a variety of forms and compositions and can be derived from naturally occurring materials, naturally occurring materials that have been synthetically modified, or synthetic materials. Examples of suitable support materials include, but are not limited to, nitrocellulose, glasses, silicas, teflons, and metals (for example, gold, platinum, and the like). Suitable materials also include polymeric materials, including plastics (for example, polytetrafluoroethylene, polypropylene, polystyrene, polycarbonate, and blends thereof, and the like). The substrate surface may include a surface modification layer, the surface modification layer having an available binding moiety (e.g. an hydroxyl moiety) for covalently binding to, e.g. the cleavable linker moiety or to a nucleotide moiety. Such surface modification layers are well known and need not be described further herein.

As mentioned above, cleavable oligonucleotide present on the substrate (e.g. at a feature of the array) is bound to the substrate via a cleavable linker moiety. The cleavable linker moiety may be cleavable by a number of different mechanisms. In certain embodiments, the cleavable linker moiety may be cleaved by light, i.e. photocleavable, or the cleavable linker moiety may be chemically cleavable, e.g., acid- or base-labile. In such embodiments, the cleavable linker moiety will comprise either a photocleavable moiety or chemically cleavable moiety. Photocleavable or photolabile moieties that may employed may include, but are not limited to: o-nitroarylmethine and arylaroylmethine, as well as derivatives thereof, and the like. Chemically cleavable moieties that may be employed may include, but are not limited to: dialkoxysilane, cyanoether, aminocarbamate, dithioacetal, disulfide, and the like.

In representative embodiments, each cleavable oligonucleotide on the array is described by the following formula:

Surface-Lc-Oligo wherein:

Lc is a cleavable linker moiety;

Oligo is an oligonucleotide bound to the surface via the cleavable linker moiety; and Surface is the surface of the substrate, e.g. an array substrate;

where each of the above features is as described herein.

In certain of these representative embodiments, only the oligonucleotide bound to the surface differs between features of the array. The oligonucleotide is typically a single-stranded nucleic acid and may be oriented such that either the 3' or 5' end of the molecule is proximal to the substrate surface. In certain embodiments, the cleavable linker moiety is bound to the surface via a short oligonucleotide, as described herein.

The methods of the present invention can be accomplished using known array synthesis apparatus, use of which is generally described below. FIG. 8 illustrates an embodiment of a typical array synthesis system 130 that provides for the deposition of nucleotide compounds to a suitable substrate (as described above), especially for the fabrication of polynucleotide arrays. The array synthesis system 130 depicted in FIG. 8 can be used to contact the array substrate with the nucleotide monomers. The array synthesis system 130 shown in FIG. 8 includes a substrate station 132 on which can be mounted a substrate 134. In addition, the array synthesis system 130 includes a dispensing head 136. The dispensing head 136 can be positioned to face the substrate station 132 by a positioning system, e.g. a 3-dimensional movable stage (an X-Y-Z stage). Once substrate station 132 has been positioned facing dispensing head 132, the positioning system will be used to scan the dispensing head 132 across the mounted substrate 134, typically line by line (although other scanning configurations could be used).

The dispensing head 132 can be of a type commonly used in an ink jet type of printer and can, for example, have multiple drop dispensing orifices communicating with one or more chambers for holding an 'ink' composition containing a nucleotide monomer. Ejectors are positioned in the one or more chambers, each opposite a corresponding orifice. For example, each ejector can be in the form of an electrical resistor operating as a heating element under control of a processor (although piezoelectric elements could be used instead). Each orifice with its associated ejector and portion of the chamber, defines a corresponding pulse jet. In this manner, application of a single electric pulse to an ejector causes a droplet to be dispensed from a corresponding orifice. In particular, the dispensing head is an industrial inkjet print head.

As is well known in the ink jet print art, the amount of fluid that is expelled in a single activation event of a pulse jet, can be controlled by changing one or more of a number of parameters, including the orifice diameter, the orifice length (thickness of the orifice member at the orifice), the size of the deposition chamber, the size of the heating element, the physical properties of the fluid, among others. The amount of fluid that is expelled during a single activation event is generally in the range about 0.1 to 1000 pL, usually about 0.5 to 500 pL and more usually about 1.0 to 250 pL. A typical velocity at which the fluid is expelled from the chamber is more than about 1 m/s, usually more than about 10 m/s, and can be as great as about 20 m/s or greater. As will be appreciated, if the orifice is in motion with respect to the receiving surface at the time an ejector is activated, the actual site of deposition of the material will not be the location that is at the moment of activation in a line-of-sight relation to the orifice, but will be a location that is predictable for the given distances and velocities. Feature sizes can be adjusted as desired, for example by using one or a desired number of pulses from a pulse jet to provide the desired final spot size, by adjusting the physical and chemical properties of the fluid (e.g. viscosity, surface tension, composition), by selecting a dispensing head having an appropriate configuration, and/or by adjusting the signal delivered to the dispensing head (e.g. to the piezoelectric element or heating element), and/or by any other known methods.

Arrays can be fabricated using drop deposition from pulse jets of precursor units (such as nucleotide monomers). Such methods are described in detail in, for example, references including U.S. Pat. No. 6,242,266, U.S. Pat. No. 6,232,072, U.S. Pat. No. 6,180,351, U.S. Pat. No. 6,171,797, U.S. Pat. No. 6,323,043, U.S. patent application Ser. No. 09/302,898 filed Apr. 30, 1999 by Caren et al., and the references cited therein.

It should be specifically understood, though, that the present disclosure is not limited to pulse jet type deposition systems. Other drop deposition methods can be used for fabrication, such as are known in the art. Also, instead of drop deposition methods, photolithographic array fabrication methods may be used. In particular, any type of array fabricating apparatus can be used to contact the substrate with nucleotide monomers and the cleavable linker moiety, including those such as described in U.S. Pat. No. 5,807,522, or an apparatus that can employ photolithographic techniques for forming arrays of moieties, such as described in U.S. Pat. No. 5,143,854 and U.S. Pat. No. 5,405,783, or any other suitable apparatus which can be used for fabricating arrays of moieties. For example, robotic devices for precisely depositing aqueous volumes onto discrete locations of a support surface, i.e., arrayers, are also commercially available from a number of vendors, including: Genetic Microsystems; Cartesian Technologies; Beecher Instruments; Genomic Solutions; and BioRobotics. Other methods and apparatus are described in U.S. Pat. Nos. 4,877,745; 5,338,688; 5,474,796; 5,449,754; 5,658,802; and 5,700,637. Patents and patent applications describing arrays of biopolymeric compounds and methods for their fabrication include: U.S. Pat. Nos. 5,242,974; 5,384,261; 5,405,783; 5,412,087; 5,424,186; 5,429,807; 5,436,327; 5,445,934; 5,472,672; 5,527,681; 5,529,756; 5,545,531; 5,554,501; 5,556,752; 5,561,071; 5,599,695; 5,624,711; 5,639,603; 5,658,734; WO 93/17126; WO 95/11995; WO 95/35505, WO 97/14706, WO 98/30575; EP 742 287; and EP 799 897. See also Beier et al. "Versatile derivatisation of solid support media for covalent bonding on DNA-microchips", Nucleic Acids Research (1999) 27: 1970-1977.

In some embodiments, after the array is made using the subject methods, as described above, the cleavable oligonucleotides are released from the surface of the array substrate to produce a solution phase mixture of oligonucleotides. In such embodiments, the array is subjected to cleavage conditions sufficient to cleave the cleavable linker moiety to release the cleavable oligonucleotides from the substrate surface. Generally, this step comprises contacting the array with an effective amount of a cleavage agent. The cleavage agent will, necessarily, be chosen in view of the particular nature of the cleavable linker moiety that is to be cleaved, such that the cleavable linker moiety is labile with respect to the chosen cleavage agent. Where the cleavable linker moiety comprises a photocleavable or photolabile group, cleavage can be effectuated by subjecting the cleavable linker moiety to light of the appropriate wavelength sufficient to cleave the cleavable linker moiety.

Likewise, for chemically cleavable moieties, the array can be contacted with a chemical capable of cleaving the cleavable linker moiety, e.g. the appropriate acid or base, depending on the nature of the chemically labile moiety. A suitable chemically cleavable linker moiety may include, for example, a chemically labile moiety selected from the following: base-cleavable moieties such as esters, particularly succinates (cleavable by, for example, ammonia or trimethylamine), quaternary ammonium salts (cleavable by, for example, diisopropylamine) and urethanes (cleavable by aqueous sodium hydroxide); acid-cleavable moieties such as benzyl alcohol derivatives (cleavable using trifluoroacetic acid), teicoplanin aglycone (cleavable by trifluoroacetic acid followed by base), acetals and thioacetals (also cleavable by trifluoroacetic acid), thioethers (cleavable, for example, by HF or cresol) and sulfonyls (cleavable by trifluoromethane sulfonic acid, trifluoroacetic acid, thioanisole, or the like); nucleophile-cleavable moieties such as phthalamide (cleavable by substituted hydrazines), esters (cleavable by, for example, aluminum trichloride), and Weinreb amide (cleavable by lithium aluminum hydride); and other types of chemically cleavable moieties, including phosphorothioate (cleavable by silver or mercuric ions) and diisopropyldialkoxysilyl (cleavable by fluoride ions). Other cleavable moieties will be apparent to those skilled in the art or are described in the pertinent literature and texts (e.g., Brown (1997) Contemporary Organic Synthesis 4(3); 216-237).

In certain embodiments, the cleavage conditions are also effective to cause base deprotection of the oligonucleotides (e.g. removal of protecting groups from the heterocyclic bases of the nucleotide subunits). Thus, base deprotection can occur concurrently with cleavage from the substrate. In other embodiments, base deprotection can occur prior to cleavage from the substrate. This allows convenient removal of the base protecting groups and washing of the array to remove the deprotection products before cleavage of the oligonucleotides from the surface. In still other embodiments, base deprotection may occur after cleavage of the oligonucleotides from the surface of the substrate. Base deprotection is typically accomplished by contacting the base-protected oligonucleotides with a deprotection agent. Deprotection of oligonucleotides and the deprotection agents used are well known and need not be described further here.

The practice of the present invention will employ, unless otherwise indicated, conventional techniques of synthetic organic chemistry, biochemistry, molecular biology, and the like, which are within the skill of the art. Such techniques are explained fully in the literature. This description puts forth how to perform the methods and use the compositions disclosed and claimed herein. Efforts have been made to ensure accuracy with respect to numbers (e.g., amounts, temperature, etc.) but some errors and deviations should be accounted for. Unless indicated otherwise, parts are parts by weight, temperature is in ° C. and pressure is at or near atmospheric. Standard temperature and pressure are defined as 20° C. and 1 atmosphere.

While the foregoing embodiments of the invention have been set forth in considerable detail for the purpose of making a complete disclosure of the invention, it will be apparent to those of skill in the art that numerous changes may be made in such details without departing from the spirit and the principles of the invention. Accordingly, the invention should be limited only by the following claims.

All patents, patent applications, and publications mentioned herein are hereby incorporated by reference in their entireties, provided that if there is a conflict in definitions the definitions explicitly set forth herein shall control.

What is claimed is:

1. An oligonucleotide array comprising a substrate having a surface and a plurality of features on the substrate, each feature of the plurality of features comprising A) a first population of oligonucleotides bound via a cleavable linker moiety to the surface, and B) a second population of oligonucleotides bound to the surface other than through said cleavable linker moiety; said first population of oligonucleotides defining an interior area of each feature; said second population of oligonucleotides defining an edge area of each feature, the edge area substantially surrounding the interior area.

2. The oligonucleotide array of claim 1, wherein the first population of oligonucleotides has a lower percentage of failure sequences than the second population of oligonucleotides.

3. The oligonucleotide array of claim 1, wherein the second population of oligonucleotides has a percentage of failure sequences that is at least 120% of the percentage of failure sequences of the first population.

4. The oligonucleotide array of claim 1, wherein the plurality of features includes at least 50 features.

5. The oligonucleotide array of claim 1, wherein the plurality of features includes at least about 200 features.

6. The oligonucleotide array of claim 1, wherein, at a given feature, the interior area is at least about 70% of the area of the total defined area of the feature.

7. The oligonucleotide array of claim 1, wherein, at a given feature, the interior area is at least about 90% of the area of the total defined area of the feature.

8. The oligonucleotide array of claim 1, wherein the edge area of each feature completely surrounds the interior area of said each feature.

9. The oligonucleotide array of claim 1, wherein the cleavable linker moiety includes a cleavable moiety selected from a photocleavable moiety and a chemically cleavable moiety.

10. The oligonucleotide array of claim 1, wherein the cleavable linker moiety includes a chemically cleavable moiety selected from an acid-cleavable moiety, a base-cleavable moiety, and a nucleophile-cleavable moiety.

11. The oligonucleotide array of claim 1, wherein the cleavable linker moiety is bound to the surface via an oligonucleotide moiety.

12. A method of synthesizing an oligonucleotide on a surface of a substrate, the method comprising,
   a) covalently binding a cleavable linker moiety to the surface, the cleavable linker moiety defining an interior area on the surface,
   b) covalently binding a nucleotide moiety to the surface, the nucleotide moiety defining a combined area on the surface, wherein the combined area includes the interior area and an edge area substantially surrounding the interior area, wherein the nucleotide moiety in the interior area is bound to the surface via the cleavable linker moiety, wherein the nucleotide moiety in the edge area is bound to the surface other than via the cleavable linker moiety; and
   c) repeating b) as necessary to result in synthesis of the oligonucleotide on the surface.

13. The method of claim 12, wherein the interior area is at least 50% of the combined area.

14. The method of claim 12, wherein the interior area is at least 70% of the combined area.

15. The method of claim 12, wherein the method is performed at each site of a plurality of sites on the surface, wherein the method results in the synthesis of an oligonucleotide at each site of the plurality of sites.

16. The method of claim 15, wherein the plurality of sites comprises at least 50 sites, wherein the method results in synthesis of at least 50 different oligonucleotides.

17. The method of claim 15, wherein the method includes using a pulse jet to deposit reagents at each site of the plurality of sites.

18. The method of claim 12, further comprising contacting the surface with a cleavage agent effective to cleave the cleavable linker moiety, said contacting being for a time and under conditions sufficient to result in cleaving the oligonucleotides from the surface.

19. The method of claim 18, said conditions also being sufficient to concurrently deprotect the oligonucleotides.

20. The method of claim 18, further comprising, prior to contacting the surface with the cleavage agent, contacting the oligonucleotide with a deprotection agent to remove protecting groups from the oligonucleotide to result in a deprotected oligonucleotide bound to the surface.

21. The method of claim 18, further comprising recovering a solution phase mixture of oligonucleotides.

* * * * *